United States Patent
Mtchedlidze

(10) Patent No.: US 7,105,189 B2
(45) Date of Patent: Sep. 12, 2006

(54) **METHOD FOR OBTAINING AN ISOLATED EXTRACT OF THE PLANT *CYCLAMEN EUROPAEUM L.* AND ITS USE AS A THERAPEUTIC AGENT**

(75) Inventor: Vakhtang Mtchedlidze, Barcelona (ES)

(73) Assignee: Hartington Business, S.L., Barcelona (ES)

( * ) Notice: Subject to any disclaimer, the term of this patent is extended or adjusted under 35 U.S.C. 154(b) by 135 days.

(21) Appl. No.: 10/470,369

(22) PCT Filed: Jan. 17, 2002

(86) PCT No.: PCT/IB02/00181

§ 371 (c)(1),
(2), (4) Date: Jul. 25, 2003

(87) PCT Pub. No.: WO02/058713

PCT Pub. Date: Aug. 1, 2002

(65) Prior Publication Data

US 2004/0076697 A1 Apr. 22, 2004

(30) Foreign Application Priority Data

Jan. 25, 2001 (ES) .......................................... 200100165

(51) Int. Cl.
*A01K 35/78* (2006.01)

(52) U.S. Cl. ....................................... 424/777; 424/725
(58) Field of Classification Search ................. 424/725, 424/777, 195.1
See application file for complete search history.

(56) References Cited

PUBLICATIONS

Friedrich et al. Laboratory Trials on the Effectiveness of Cyclamin Against Arion Lustanicus Mab. (Gastropoda:Arionidae) and other snails, Zeitschrift fur Angewandte Zoologie (1993) vol. 80, No. 3, English Abstract Only.*
Friedrich et al. Laboratory Trials on the Effectiveness of Cyclamin against Arion Lusitanicus Mab. (Gastropoda:Arionidae) and other snails, Zeitschrift fur Angewandte Zoologie (1994) vol. 80, No. 3, English Abstract Only.*
Taylor et al. Taking the Case; Whole Health Now, URL <http://www.wholehealthnow.com/homeopathy—pro/wt15a.html> pp. 1–2.*
Cyclamen Purpurascens; URL, <http://ww.riva.ca/Cyclamen/purpurascens.html> pp. 1–3.*
Issacson, G. "Sinusitis in Childhood". Pediatr Clin North Am. Dec. 1996;43(6):1297–318.
Zeiger, RS. "Prospects for Ancillary Treatment of Sinusitis in the 1990's". J Allergy Clin Immunol. Sep. 1992;90(3 Pt 2):478–95.
Wald, Ellen R. "Chronic Sinusitis in Children". *The Journal of Pediatrics*, Sep. 1995, vol. 127, No. 3.

* cited by examiner

*Primary Examiner*—Patricia Leith
(74) *Attorney, Agent, or Firm*—Steinberg & Raskin, P.C.

(57) ABSTRACT

The invention relates to a procedure for obtaining an isolated extract of the plant *Cyclamen europaeum L.* and to its use as a therapeutic agent. In particular, it relates to the use of the isolated extract for preparing a medicament for treating sinusitis. This invention also relates to a method for extracting the isolated extract by aqueous extration and by alcoholic extraction.

6 Claims, 2 Drawing Sheets

METHOD FOR OBTAINING AN ISOLATED EXTRACT OF THE PLANT *CYCLAMEN EUROPAEUM L.* AND ITS USE AS A THERAPEUTIC AGENT

FIELD OF THE INVENTION

This invention relates to a procedure for obtaining an isolated extract of the plant *Cyclamen europaeum L.* and to its use as a therapeutic agent. In particular, it relates to the use of said isolated extract for preparing a medicament for treating sinusitis.

This invention also relates to a method for extracting said isolated extract by aqueous extraction and by alcoholic extraction.

BACKGROUND OF THE INVENTION

Known in the state of the art are various methods for treating inflammation of the mucous membrane or of the paranasal sinuses, in particular sinusitis. However, current procedures for treating sinusitis, both acute and chronic, centre above all on three basic problems to which a solution is to a greater or lesser degree decisive as regards the efficacy and duration of the treatment. These problems are: re-establishing ventilation and normal draining of the paranasal sinuses, halting the process of inflammation and swelling of the mucous membrane and combating the infectious microflora.

Said illnesses are often treated in a conservative way, involving the use of antimicrobic products which are not always effective, since in some cases they stimulate resistance to the pathogenic microflora of these products which, in their turn, are not sufficiently innocuous.

In the first phases of acute sinusitis these treatment procedures provide for oral administration of first-line antibiotics such as ampicillin and amoxicillin. If these prove to be ineffective, then amoxicillin and clavulanic acid or cephalosporins of generations II and III are prescribed [Ellen R. Wald, MD, *Chronic sinusitis in children. Journal of Pediatrics*, 1995, 127 (3) 339; *Inexpensive Antibiotics are as Effective as Newer, More Expensive Ones in Treating Acute Bacterial Sinusitis.* Press Release, Mar. 23, 1999. Agency for Health Care Policy and Research, Rockville, Md.; and Glenn Isaacson, MD, FAAP, FACS, *Sinusitis in Childhood,* Ped. Clin. of N Am., 1996, 43(6):1305].

The role of antibiotics in treatments for chronic sinusitis is smaller than in the case of acute sinusitis, since the main purpose is to re-establish normal ventilation of the ethmoidal sinuses, to which end local-action decongestants are applied, which, accompanied by antibiotic therapy, eliminate the swelling of the mucous membrane, improve drainage and re-establish the functioning of the eustachian tube and of the ethmoidal sinuses of the nose. However, the application of local decongestants for a period of more than five days can cause medicament-induced renitis (Zeiger, R. S., *Prospects for ancillary treatment of sinusitis in the 1990s.* J. Allergy Clin. Immunol., 1992, 90:478). In the case of pathologies in chronic state recourse is had to surgical intervention, cleaning the paranasal sinuses by means of direct puncturing.

In view of all that has been stated above, the treatment of acute or chronic sinusitis is a long and complicated process which, in function of its gravity, can take several years. Furthermore, the sources consulted were unable to confirm the total efficacy of the treatments applied in normal practice.

The possible solution to the problems of sinusitis is to be found by seeking and studying new methods of treatment.

Known in the state of the art is the utilisation of alternative treatments which make use of biologically active substances of natural origin. However, there does not exist in the state of the art any bibliography on the vast majority of substances of natural origin.

The wild plant *Cyclamen europaeum L.*, in this invention called cyclamen plant, belongs to the Primulaceae family, and although it is a very popular plant in many countries of the world, its use is limited to decorative purposes. Little information is available about its medicinal properties, and there is reference only to use of the juice or powder obtained from the plant for treating headache.

On the basis of the state of the art, therefore, there exists no product as an alternative to antibiotics for treating sinusitis.

OBJECTS AND SUMMARY OF THE INVENTION

This invention resolves the disadvantages mentioned above, while it also provides other advantages which will be described below.

A first objective of this invention is a method for obtaining an isolated extract of the wild plant *Cyclamen europaeum L.*

A second objective of this invention is the utilisation of an isolated extract according to the invention in order to manufacture a medicament for treating sinusitis.

In accordance with the first objective of the invention, a method has been developed for obtaining an isolated extract of the wild plant *Cyclamen europaeum L.*, which is characterised in that an aqueous extraction is carried out which comprises:

a) a first stage of pressing of the previously cleaned and prepared tuber;

b) a second stage of purification of the liquid fraction obtained following the pressing, which includes:

b-i) the addition of ethyl alcohol to said liquid fraction;

b-ii) its subsequent storage in a refrigeration chamber at a temperature between 2° C. and 25° C., preferably between 4° C. and 8° C., for 10–48 hours, preferably for 18–20 hours, and;

b-iii) finally, filtering.

Preferably, the filtering stage b-iii) is carried out in two steps: first through a primary purification filter, and then through a fine-pore bactericidal filter, at a pressure of 0.25±0.005 MPa.

Advantageously, an additional stage of pressing is carried out, for the solid fraction of residues obtained after a first pressing still contains a large quantity of biologically active substances, recovery of which represents an increased yield from the method on the basis of which the isolated extract of the invention can be obtained. Said additional stage comprises:

a-i) preparing the solid fraction, residues from he pressing, by means of addition of water in a ratio of 1:0.5–1.8, preferably 1:0.64–0.66. The value 1 refers to the weight in grams of the tuber before pressing, while the values 0.5–1.8 or 0.64–0.66 refer to the volume of water added to the solid fraction obtained after the first pressing;

a-ii) thermostat-controlling the prepared mass to a temperature of between 20° C. and 80° C., preferably between 60° C. and 70° C., for 1 hour and then carrying out a second pressing; and a-iii) finally, in a mixing reactor, mixing the liquid fraction from the second pressing, also called extract of residues, with the liquid fraction from the first pressing, also called juice.

From this point the procedure continues with stage b) of purification of the liquid fraction described above (see FIG. 1).

Optionally, a method has been developed for obtaining an isolated extract of the wild plant *Cyclamen europaeum L.* which is characterised in that an alcoholic extraction is carried out which comprises:

a) a first stage of trituration of the previously cleaned and prepared tuber;

b) a second stage of extraction of the biologically active substances, which comprises:

b-i) the addition of an alcohol, preferably ethanol, to the triturate of tubers in a ratio by volume of tuber/solvent of between 1:1 and 1:5, preferably 1:3;

b-ii) the prepared mass is brought to boiling point in alcohol and kept there for 1 hour, before the alcoholic extraction is carried out;

c) a third stage of purification of the alcoholic extraction, which comprises:

c-i) the addition of a sorbent in order to remove the colorants from the alcoholic extract in a ratio of mass of raw material to mass of sorbent of between 30:0.5 and 30:2, preferably 30:1.

c-ii) purification in refrigerant under reflux; and c-iii) finally, filtering.

Advantageously, a second extraction b-iii) is carried out under the same conditions, from which approximately 20% of the total saponins is obtained. In this case, the alcoholic extracts of the first and second extraction are mixed in a common alcoholic extraction mixer before proceeding to the purification stage (see FIG. 2).

The sorbent used in the purification by alcoholic extraction is selected from among activated carbon, silica gel, clay and grade II aluminium oxide, the best results being obtained with grade II aluminium oxide.

A reference measurement of the quantity of biologically active substances extracted from the plant is drawn up on the basis of the haemolytic index. The tubers of the cyclamen species contain a cyclamen-saponin which hydrolyses to form cyclamyrethin sapogenin and carbohydrates (glucoses and arabinose). Apart from saponin, sugars (glucose, fructose and other polysaccharides) have been detected, together with resinous substances, colorants and phenolic compounds. The water content in the tubers exceeds 70%.

The haemolytic index indices the ratio of saponins extracted. Below a haemolytic index of 300 units there is no commercial advantage in repeating the pressing process or obtaining a second extract, for after two stages of pressing or extraction up to 96–98% of biologically active substances in the plant have been obtained.

After the first pressing or obtaining of the first extract, the liquid fraction has a haemolytic index of between 8,000 and 12,000 units, and after the second pressing or obtaining of the second extract the liquid fraction has a haemolytic index of between 300 and 500 units. Additional stages of pressing or obtaining of a third extract will not therefore permit a liquid fraction to be obtained with haemolytic index values suitable from the economic point of view.

Thus, the isolated extract obtained presents a haemolytic index of between 6,000 and 12,000 and an acidity value of between 5.0 and 6.8.

A second objective of this invention is the utilisation of a an isolated extract obtained according to any of the methods described for the manufacturing of a medicament for treating sinusitis.

For this purpose, the invention proposes an isolated extract of the wild plant *Cyclamen europaeum L.* which includes a higher concentration of saponins but which also includes sugars (glucose, fructose and other polysaccharides), resinous substances and colorants, phenolic complexes and other additives not detected but which nevertheless confer upon the isolated extract therapeutic properties suitable for the manufacturing of a medicament for treating sinusitis.

BRIEF DESCRIPTION OF THE DRAWINGS

For a better understanding of all that has been outlined, two figures have been attached which, schematically and solely by way of non-restrictive example, show a practical case of embodiment.

Figure 1:
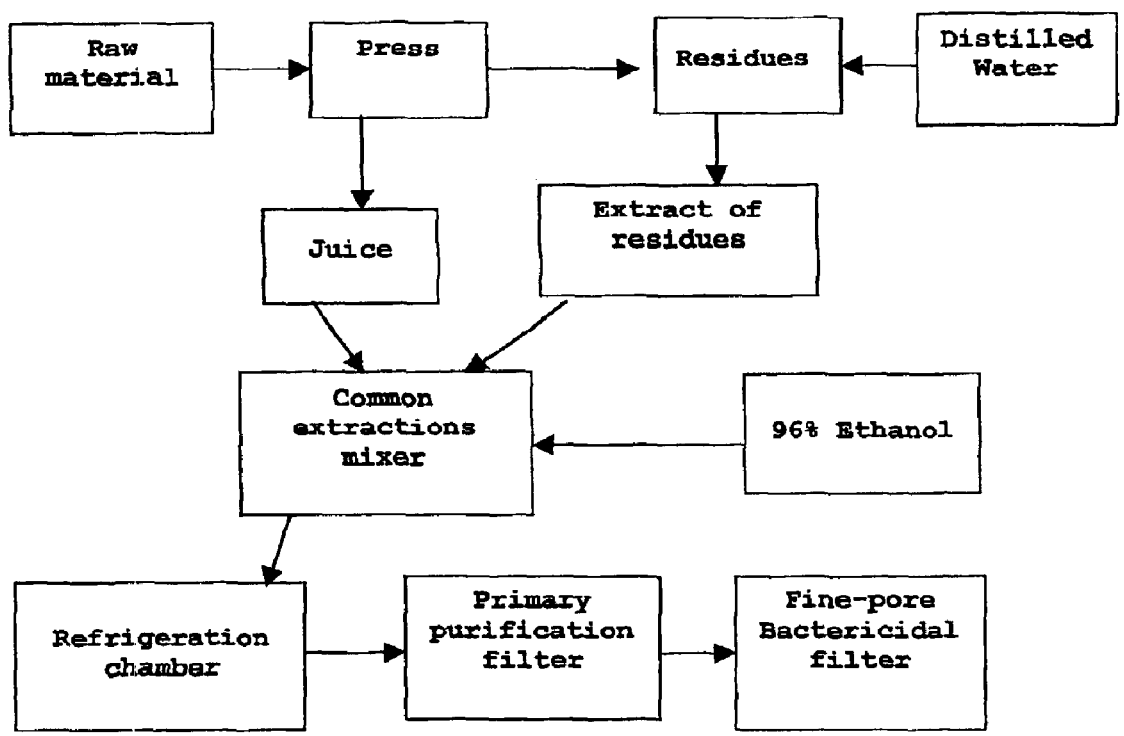
FIG. 1 shows a flow diagram of the method of the invention for obtaining an isolated extract by aqueous extraction.
Figure 2:
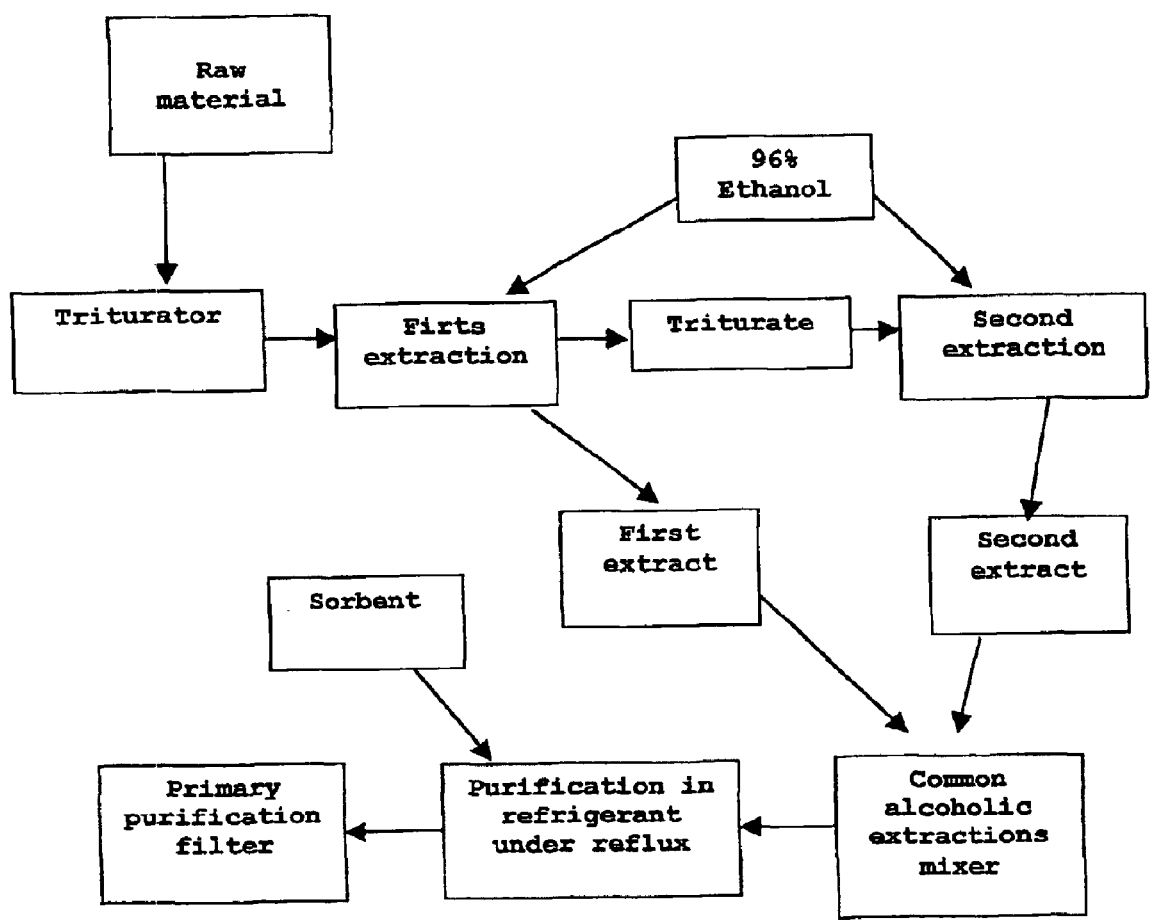
FIG. 2 shows a flow diagram of the method of the invention for obtaining an isolated extract by alcoholic extraction.

There follows below a more detailed description of the method for obtaining an isolated extract by means of aqueous extraction and by means of alcoholic extraction.

DETAILED DESCRIPTION OF THE INVENTION

There follows a description of a preferred embodiment of the method for obtaining an isloated extract of the wild plant *Cyclamen Europaeum L.* by aqueous extraction.

In a first embodiment of the invention, the tuber of the cyclamen plant is cleaned with running tap water until the earth, sand and other impurities have been completely removed from it, following which it is scrubbed with a brush in order to remove the microparticles of earth, sand, etc. The tubers are then washed with distilled water and left to dry in the air. The dry tubers are then placed in a bath and covered entirely with 95% ethanol and left for one hour.

Once clean, the tubers are placed in the press, in which the juice is expressed mechanically. The percentage of juice or liquid fraction obtained varies between 55 and 65% in relation to the solid mass or solid fraction after pressing.

Owing to the high haemolytic activity of the residues produced, extraction of the saponins is carried out with desalted water. A suitable ratio of solid mass and volume of liquid needed for extraction was determined in the course of the research to be 1:0.64–0.66.

That ratio was found to provide the greatest haemolytic activity of the samples. The optimum temperatures for extraction are between 60 and 70° C., while the extraction time was 60 minutes. Application of said temperatures and time was observed to lead to maximum change of the saponins in the aqueous extraction. The same parameters were also optimum from the technological point of view, given that once a temperature of 80° C. is reached the extract becomes viscous and difficult to filter due to partial hydrolysis of the polysaccharides, while prolonging the time induces an increase in exit of the saponins.

Secondary extraction of the residues by water was found to provide a haemolytic index of 300–500 units, suggesting a need for one extraction only.

Once the extraction has been carried out, the mass of residues is deposited in the press and is subjected to expression. The juice and the extract of the residues are mixed in the reactor with a mixer, providing common extractions therefrom.

The aqueous extractions obtained (juice of tubers+extract from the residues), like the end products, contain major disposable impurities and therefore require additional cleaning.

Most of the impurities can be eliminated by adding to the extractions 15% of ethyl alcohol at 96% and then keeping in the refrigeration chamber for 18–20 hours. Once that time has elapsed, the extractions are filtered through the primary purification filter, and then the fine-pore bactericidal filter. This last sterilised filtration of the resulting extractions is carried out at a pressure of 0.25±0.005 MPa.

The filtrations provide a transparent solution which remains stable for two months when kept in a refrigeration chamber at a temperature of 4–8° C. This solution serves as the base substance for making a medicament for treating sinusitis.

In a second embodiment of the invention, a method is disclosed for obtaining an isolated extract of the wild plant *Cyclamen europaeum L.* by alcoholic extraction.

Once clean and prepared, the tubers are cut into small pieces, placed in a jar and covered with 96% ethyl alcohol in a proportion of solid mass (raw material) and volume of solvent of 1:3, respectively. The mixture is heated until the solvent boils and is then left for 60 minutes. A second extraction is then carried out under the same conditions, from which an average of 20% of the total saponins is obtained.

The alcoholic extractions obtained from the first and second extractions are combined and purified by refrigerant under reflux to eliminate the colorants.

The purification is carried out with grade II aluminium oxide at a temperature of 40–50° C. and is repeated three times, for 15–20 minutes each time. The optimum proportion of the mass of raw material to mass of sorbent is 30:1, respectively.

The purified extract serves as the base substance for production of a medicament for treating sinusitis. This extract remains stable for two months when kept in a refrigeration chamber at a temperature of 4–8° C.

Pharmacological Results

Study of the pharmacological properties of the isolated extract of the invention has shown that application of its light concentrates produces reflexive secretion from the nasal cavity. With said extract it is possible to obtain solutions of different concentrations, or in other words to personalise the dosage.

Study of the reflexive reaction, carried out by placing 2–3 drops of a medicament prepared with the isolated extract of the invention in the nasal cavity of rabbits and dogs has shown that neither the latent reaction period nor the duration of the secretion present alterations of any kind, irrespective of whether the preparation is administered daily (every 24 hours) or on alternate days.

The information from the histological study shows that application of the preparation does not cause side-effects of irritation, and still less inflammation of the mucous membrane.

A second administration into the nasal cavity of the recommended doses of a preparation of the isolated extract of the invention does not cause adverse alterations of the general state or behaviour of the animals.

The therapeutic action of a preparation that includes the isolated extract of the invention is based on stimulation of the secretive activity of the integumentary epithelium of the mucous membrane in general, together with the serum and submucous glands, which facilitates an intense draining of the paranasal sinuses. According to histological information, the optimum period for the second intranasal administration is 48 hours.

Concentrations of the preparation retain their efficacy in solutions of between 1:100 and 1:500.

The conditions of application of the preparation, together with the characteristics of the reaction of administration thereof, practically exclude any possibility of it being absorbed from the surface of the mucous membrane and producing an undesirable systemic action.

Toxicological Study

The systemic toxic properties of the isolated extract and of the medicament containing it have been studied in albino mice and rats by means of intraperitoneal, intravenous and oral administration, given that it is impossible to administer sufficiently large doses intranasally, that is, the method recommended for the clinical trial.

The toxic manifestations in all the methods of administration were generally those inherent to the saponins: a generalised depression of the central nervous system and delayed (up to 3 days) mortality in the event of intra-abdominal and oral administration; intravascular haemolysis and immediate mortality in the event of intravenous administration; localised irritant action in relation to the mucous membranes.

The lethal single doses of oral administration, applied to mice, are:

(a) Alcoholic extract: $LD50$—1337.7±23 mg/kg; $LD84$—1894 mg/kg, $LD16$—781 mg/kg;

(b) Aqueous extract: $LD50$—1466.5±37 mg/kg; $LD84$—2107 mg/kg, $LD16$—826 mg/kg;

(c) Medicament: $LD50$—2386.84±85 mg/kg; $LD84$—3852 mg/kg, $LD16$—920 mg/kg;

According to the general toxicological classification of the $LD50$ indices, the isolated extract and the medicament that contain it pertain to the elements of moderate or slight toxicity with localised irritant action of moderate extent.

The single non-toxic, non-effective dose of the medicament applied to mice is 10 mg/kg, that is, $\frac{1}{250}$ $LD50$, and exceeds the maximum single therapeutic dose (0.03 mg/kg) recommended for clinical trials by approximately 350 times.

The subtoxic toxicity of the non-toxic dose of the medicament was studied in mice in an experiment on therapeutic intranasal application carried out over the course of two weeks, and shows the cases of undesired penetration of the preparation from the nasal cavity into the stomach.

The second oral administration of the medicament for 14 days in a dose of 10 mg/kg was totally innocuous for the mice.

The innocuousness of the isolated extract and of the medicament administered five times has been shown by the results of the study of the specific pharmacological activity of these preparations in the event of applying maximum "therapeutic" concentrations.

The localised irritant action of the medicament shows itself to the greatest extent with the conjunctive tissue but was not detected in the mucous membrane of the stomach, while the mucous membrane of the nasal cavity probably lies between these two as regards degree of irritability.

The clinical trials of the medicament in solutions of 1:100 to 1:500, which is approximately equivalent to $\frac{1}{350}$–$\frac{1}{500}$ of the "non-toxic" oral dose applied to mice, can be considered totally innocuous, especially if account is taken of it being practically impossible for the preparation to be absorbed or ingested from the nasal cavity.

Despite the fact that a specific embodiment of this invention has been described and shown, it is obvious that an expert in the subject would be able to introduce variations and modifications, or replace the details by others that are technically equivalent, without departing from the sphere of protection defined by the attached claims.

What is claimed is:

1. A method for obtaining an extract of the wild plant *Cyclamen europaeum L.* for treating sinusitis, which comprises:
   a) cleaning a tuber *Cyclamen europaeum L.*;
   b) pressing the cleaned tuber of *Cyclamen europaeum L.* to obtain a first liquid fraction and a solid fraction;
   c) adding water to the solid fraction in ration of 1:0.5–1.8;
   d) thermostat-controlling the solid fraction of part (c) to a temperature of between 20° C. and 80° C.;
   e) pressing the solid fraction with added water of part (c) to obtain a second liquid fraction;
   f) mixing the first liquid fraction with the second liquid fraction in a mixing reactor to obtain a mixture of liquid fractions;
   g) purifying the mixture of liquid fractions of part (f) comprising:
   h) adding an alcohol to the mixture of part (f) and storing it in a refrigeration chamber; and
   i) filtering the mixture of part (f) to obtain said extract of *Cyclamen europaeum L.*

2. The method as claimed in claim 1, wherein said storage is carried out at a temperature between 2° C. and 25° C. for 10–48 hours.

3. The method as claimed in claim 2, wherein said storage is carried out at a temperature between 4° C. and 8° C. for 18–20 hours.

4. The method as claimed in claim 1, wherein said filtering is carried out in two steps: first, through a primary purification filter and, through a fine-pore bactericidal filter, at a pressure of 0.25±0.005 MPa.

5. The method as claimed in claim 1, wherein in part (c) water is added in a ratio of 1:0.64–0.66.

6. The method as claimed in claim 1, wherein in part (d) thermostat-controlling the solid fraction is carried out to a temperature from 60° C. to 70° C. for 1 hour.

* * * * *